United States Patent [19]

Suciu et al.

[11] Patent Number: 4,510,258

[45] Date of Patent: Apr. 9, 1985

[54] CATALYSTS CONTAINING MIXED OXIDES OF VANADIUM AND PHOSPHORUS

[75] Inventors: George D. Suciu, Ridgewood, N.J.; Giancarlo Stefani; Carlo Fumagalli, both of Bergamo, Italy

[73] Assignees: The Lummus Company, Bloomfield, N.J.; Alusuisse Italia S.p.A Milan, Italy

[21] Appl. No.: 523,931

[22] Filed: Aug. 17, 1983

[51] Int. Cl.³ .................. B01J 27/14; C07D 307/60
[52] U.S. Cl. ................................ 502/209; 549/259
[58] Field of Search ................................. 502/209

[56]       References Cited
       U.S. PATENT DOCUMENTS

| | | | |
|---|---|---|---|
| 3,912,763 | 10/1975 | Farha, Jr. et al. | 502/209 X |
| 3,975,300 | 8/1976 | Buness | 502/209 |
| 4,085,122 | 4/1978 | Slefoni et al. | 549/259 |
| 4,092,269 | 5/1978 | Mount et al. | 502/209 |
| 4,253,988 | 3/1981 | Mount et al. | 502/209 |
| 4,276,222 | 6/1981 | Mount et al. | 502/209 |
| 4,294,722 | 10/1981 | Bremer et al. | 502/209 |
| 4,304,723 | 12/1981 | Freerks | 549/259 |
| 4,317,778 | 3/1982 | Blum et al. | 549/259 |
| 4,333,853 | 6/1982 | Milberger et al. | 502/209 |
| 4,351,773 | 9/1982 | Milberger et al. | 549/259 |
| 4,359,405 | 11/1982 | Mount et al. | 502/209 |
| 4,412,940 | 11/1983 | Mount et al. | 502/209 |

*Primary Examiner*—William G. Wright
*Attorney, Agent, or Firm*—Elliot M. Olstein

[57]           ABSTRACT

Mixed oxide catalyst of vanadium and phosphorus prepared by a procedure including pretreating the dried catalyst precursor of the said mixed oxides in finely divided form with an acid solution.

21 Claims, No Drawings

CATALYSTS CONTAINING MIXED OXIDES OF VANADIUM AND PHOSPHORUS

This invention relates to mixed oxide catalysts, and more particularly, to a catalyst comprised of mixed oxides of vanadium and phosphorus, and the preparation and use thereof.

The production of a catalyst comprised of mixed oxides of vanadium and phosphorus is well known in the art, as exemplified by U.S. Pat. Nos. 3,815,892; 4,085,122; 4,304,723; 4,317,778; and 4,351,773. Such catalysts are oxidation catalysts, and are particularly suitable for the preparation of maleic anhydride.

In many cases, it is desirable to use such a catalyst in a fluidized bed. As a result, there is a need for a catalyst comprised of mixed oxides of vanadium and phosphorus which not only has the requisite catalyst activity, but which is also resistant to attrition in a fluidized bed.

In accordance with one aspect of the present invention, there is provided a catalyst comprised of mixed oxides of vanadium and phosphorus which has the requisite catalyst activity, and which has an increased resistance to attrition.

More particularly, in accordance with one aspect of the present invention, there is provided a catalyst comprised of mixed oxides of vanadium and phosphorus which has been prepared by treating a finely divided solid catalyst precursor comprising mixed oxides of vanadium and phosphorus with an acid solution, followed by drying of the treated catalyst to produce a mixed oxide catalyst having an increased resistance to attrition. Applicant has found that by treating such a catalyst precursor with an acid, followed by drying of the catalyst, the treated particles agglomerate to produce larger catalyst particles and such catalyst particles of increased size have an increased resistance to attrition.

The acid which is used for treating the finely divided catalyst is an acid which does not adversely affect the valency state of the vanadium in the catalyst. The acid is preferably a phosphoric acid (e.g., meta-, ortho-, pyro-, poly-, $P_2O_5$) in that phosphorus is a component of the catalyst; however, as hereinafter indicated, the amount of phosphoric acid used must be regulated so as to not adversely affect the ratio of phosphorus to vanadium in the catalyst. Although phosphoric acid is preferred, it is possible to use hydrochloric acid, oxalic acid, tartaric acid, etc.; however, the use of acids other than a phosphoric acid may necessitate an additional step to remove the acid from the catalyst after the treatment.

The starting material which is employed in producing a mixed oxide catalyst in accordance with one aspect of the present invention is a catalyst precursor comprised of mixed oxides of vanadium and phosphorus, prepared by procedures generally known in the art, which employ either an aqueous or organic reaction medium. Such catalyst precursor is recovered from the reaction medium by procedures known in the art, such as heating to dryness, filtration and the like.

In accordance with a preferred aspect of the invention, the solid catalyst precursor, comprised of mixed oxides of vanadium and phosphorus, is ground to produce particles having a size of less than 10 microns, and preferably less than 3 microns, preferably by a wet process, such as in a ball mill or high intensity attritor. The grinding or comminuting is accomplished as generally known in the art, with the temperature generally ranging from 20° C. to 100° C., and preferably being in the order of from 50° C. to 95° C.

In this portion of the operation, if desired, additives of a type known in the art to be suitable for use in such a mixed oxide catalyst may be added. Thus, for example, in accordance with a preferred aspect, a hydroxide or other suitable salt of a group IV-B metal, and in particular, zirconium and titanium, may be added to the catalyst at this time.

A catalyst precursor is then recovered from the slurry (if a wet process is used) by vaporizing the water, with spray drying being a preferred technique.

The dry catalyst, which as known in the art predominantly contains vanadium in the tetravalent state, is then calcined in order to convert a portion of the vanadium to the pentavalent state, as well as to remove water of hydration. In general, a partial oxidation of vanadium to the pentavalent state and the removal of water of hydration is accomplished in two separate stages. Thus, for example, the dry catalyst precursor may be heated in the presence of oxygen, preferably as air, at a temperature in the order of from 150° C. to 350° C. in order to convert a portion of the vanadium to the pentavalent state. Such heating is continued for a period of time sufficient to accomplish such results. Such precalcined catalyst is then heated in a non-oxidizing atmosphere to a higher temperature; for example, a temperature in the order of from 400° C. to 550° C., for a duration of time to remove the water of hydration. Although the temperature of 400° C. to 550° C. has been provided for purposes of illustration, it should be apparent that the specific temperature which is employed is dependent upon the method which was originally used for producing the catalyst precursor.

Alternatively, partial oxidation of the catalyst and removal of the water of hydration can be accomplished in a single step by appropriate control of the heating range, nature of the non-oxidizing atmosphere (for example, a mixture of inert gas and oxygen), by procedures known in the art.

The calcined precursor is then comminuted to produce finely divided catalyst, and in particular, a catalyst having a particle size of less than 10 microns, preferably less than 3 microns. As in the previous grinding step, such grinding is preferably accomplished in a wet state, by use of appropriate apparatus, such as a high intensity attritor or ball mill, etc.

During the grinding operation or after the grinding (particle size less than 10 microns), the catalyst is treated with an acid of the type hereinabove described.

Although the invention is not limited by any theoretical reasons, it is believed that the treatment of the finely divided catalyst (less than 10 microns) with acid results in some solubilization of the catalyst surface, and upon subsequent drying, there is improved binding of particles to each other to increase the resistance to attrition.

As hereinabove indicated, the preferred acid for treating the precursor is a phosphoric acid, and in such a case, the amount of phosphorus in the precursor must be coordinated with the amount of phosphoric acid used in the treatment so that there is sufficient phosphoric acid to accomplish solubilization of the catalyst precursor without adversely affecting the ratio of phosphorus to vanadium in the final catalyst.

In general, it is desired that the final mixed oxide catalyst include phosphorus and vanadium in an amount such that the ratio of phosphorus to vanadium is from 2:1 to 1:1, with the best results being achieved when the phosphorus to vanadium ratio is in the order from 1:1 to 1.8:1, and most preferably from 1:1 to 1.3:1.

After treatment with the acid, the treated catalyst particles are dried, resulting in agglomeration of the particles to produce larger particles having an increased resistance to attrition. In general, the larger particles have an average particle size of at least 40 microns, and in most cases, the average particle size does not exceed 200 microns. It is to be understood, however, that the catalyst may be agglomerated into larger particles.

The catalyst is generally formed into a spherical shape in that such shape is preferred for fluidized beds. In most cases, the catalyst is dried into microspherical particles (for example, a size of 40 to 200 microns), with the formation of such microspheres being easily accomplished by the use of a spray drying technique.

After drying of the treated catalyst, the catalyst is generally calcined prior to use thereof.

In accordance with another embodiment, which is less preferred, the first calcination step may be eliminated, and in such case, the uncalcined catalyst precursor is treated with phosphoric acid, followed by drying and calcination. It has been found that although there is an increase in the attrition resistance, as compared to an untreated catalyst, the omission of the calcination step, prior to the treatment with phosphoric acid, produces a catalyst which is less resistant to attrition than a catalyst which is calcined prior to the treatment with phosphoric acid.

Although the hereinabove described process wherein the catalyst precursor is calcined to both partially oxidize the vanadium and remove water of hydration, followed by acid treatment of finely divided catalyst and drying increases the resistance to attrition, there is some loss of catalyst activity, as compared to treatment of the uncalcined catalyst.

Accordingly, in accordance with a particularly preferred embodiment, a mixture of calcined and uncalcined precursor, in finely divided form, is treated with acid, as hereinabove described. Since treatment of uncalcined catalyst with acid retains activity, with some increase in attrition resistance, and acid treatment of calcined catalyst greatly increases attrition resistance, with some loss of catalyst activity, in accordance with the preferred embodiment, a mixture of calcined and uncalcined catalyst, in finely divided form, is treated with acid, followed by drying to produce a final catalyst having a desired balance of attrition resistance and catalyst activity. Thus, an increase in the quantity of uncalcined catalyst in the mixture which is treated increases activity and reduces resistance to attrition and vice versa. By varying the ratio, there can be achieved a desired balance between catalyst activity and resistance to attrition. In general, if a mixture is used, the ratio of calcined precursor to uncalcined precursor is from 10:1 to 1:10, preferably from 4:1 to 1:4.

As hereinabove indicated, the catalyst precursor comprised of mixed oxides of vanadium and phosphorus may be prepared by procedures generally known in the art, including reaction in either aqueous or organic medium. Thus, as known in the art, the vanadium component of the catalyst precursor may be obtained by use of either a tetravalent vanadium salt or by the use of a pentavalent vanadium compound which can be reduced in situ to a tetravalent vanadium salt.

As representative examples of suitable compounds, there may be mentioned vanadium tetrachloride, vanadium dioxide, vanadium oxydibromide, etc., all of which are tetravalent salts; and vanadium pentoxide (which is preferred), vanadium oxytribromide, vanadium oxytrichloride, etc., all of which are pentavalent vanadium compounds.

As the source of phosphorus in the catalyst precursor, there may be employed phosphorus acid, phosphoric acid, such as metaphosphoric acid, triphosphoric acid, pyrophosphoric acid, and the like. As known in the art, vanadium and phosphorus compounds are reacted in either an aqueous or organic system, under non-oxidizing conditions so as to maintain the vanadium in the tetravalent form, or in the alternative, under reducing conditions, when a pentavalent vanadium compound is employed so as to convert the vanadium to tetravalent form, in situ.

In general, as known in the art, the phosphorus and vanadium compounds are reacted in an acid solution, preferably one which has reducing properties, such as hydrochloric acid.

The procedures for producing the catalyst precursor comprised of mixed oxides of vanadium and potassium are well known in the art, for example, as described in U.S. Pat. No. 4,085,122, and the other patents and, therefore, no further details in this respect are deemed necessry for a complete understanding of the invention.

Although the catalyst produced in accordance with the invention may be employed as a catalyst in a wide variety of oxidation reactions, the catalyst is particularly suitable for producing maleic anhydride, and in particular, in a fluidized bed.

As generally known in the art, n-butane may be oxidized to maleic anhydride in the presence of fluidized catalyst by reaction of n-butane with oxygen at a temperature in the order of from 320° C. to 500° C., and preferably from 360° C. to 460° C. The reaction is accomplished with an excess of oxygen, with the oxygen preferably being provided in combination with an inert gas, such as in air, with the oxygen to butane ratio ranging from 15:1 to 1:1 and preferably from 10:1 to 2:1 by weight. It is to be understood, however, that although butane is a preferred feed, as known in the art, saturated or unsaturated $C_4$ to $C_{10}$ hydrocarbon or mixtures thereof are generally suitable as feeds for producing maleic anhydride; e.g., n-butanes, 1,3-butadiene, or a $C_4$ cut from a refinery, with n-butane being particularly preferred.

In the following examples, the resistance to attrition of a catalyst was tested by a procedure similar to the one described in U.S. Pat. No. 4,101,116 (column 3). In the test, the fines (particles with sizes below 20 microns), generated by one jet of air with close to sonic velocity, and which impinges vertically upwards into a known amount of catalyst, are retained and weighed between the 30th and 90th minute from the beginning of the test. The fines are recovered, as described in U.S. Pat. No. 4,010,116, and the figures representing the attrition rate (AR) are calculated as weight percent fines generated in the period of one hour (30th to 90th minute) from the particular catalyst tested and at the conditions specified.

Although there is no quantitative correlation between the attrition rate as calculated herein, and the manner in which a catalyst will actually perform in a plant, in order to provide a frame of reference as to a desired resistance to attrition, catalysts (other than unsupported mixed oxides of vanadium and phosphorus) which are commercially used and known to be resistant to attrition in a fluidized bed were tested by the same procedure in order to determine the attrition resistance of such catalysts. In testing three different commercially available catalysts of such type, it was found that the AR ranges from 2 to 26, with a lower value for the AR signifying a more attrition resistant catalyst.

EXAMPLE 1

One thousand grams of dried complex of mixed oxide of vanadium and phosphorus (VPO) prepared according to U.S. Pat. No. 4,085,122 (Example 1) was mixed with 1000 g $H_2O$ and 235 g of a paste of hydrated zirconium hydroxide (approx. 85 wt% water content) and introduced into a high intensity ball mill. The "Attritor 1-S" laboratory model manufactured by Union Process, Inc., Akron, Ohio was used during this work.

The grinding media consisted of 40 lbs. of stainless steel balls with 3/16" diameter.

1. Grinding-1—The operation was carried out for one hour at rotation velocity of the shaft of approximately 370 rpm. The dissipation of mechanical energy caused the temperature of the medium to increase within one hour to approximately 80° C. although no heating medium was circulated through the jacket of the attritor. A sample of the slurry showed that no particles existed with diameters larger than 0.5 μm.
2. Recovery—The slurry was removed from the attritor and spray dried. The microspherical material with diameters of 40-200 μm was recovered and processed further.
3. Calcination—The spray-dried product was heated gradually to 450° C. and maintained at this temperature for 6 hours. An atmosphere of $N_2$ was maintained in the oven, during the calcination.
4. Grinding-2—One thousand grams of material recovered from the previous step were mixed with 1000 g $H_2O$ and introduced into the attritor. No cooling water was circulated through the jacket. After an initial grinding period to reduce particle size, a solution of 47 g $H_3PO_4$ (85%) in 300 g of water was added. After three hours of operation, a sample of the slurry showed that all particles had sizes under 0.5 μm.
5. The slurry was drained from the attritor and spray dried. The microspherical material with diameters of 40-200 μm was recovered and submitted to step (6) which is calcination at the conditions described for step (3). In order to evaluate the effects of the above treatment, samples of microspherical material were recovered after both steps (3) and (6) and were submitted to the attrition test described earlier. The results are presented in Table 1 (1 and 1A, respectively).

EXAMPLE 2

The activity of the catalysts was tested in a fluid bed reactor. The reactor was made of a Pyrex tube (4.6 cmID) provided at the lower part with a frit of sintered glass and placed inside a vertical cylinder heated electrically. Air and n-butane are metered via mass flow controllers and fed below the frit. The reactor effluent is water washed in two bubblers in series and its flow rate is measured. The composition of the feed and vent gases were determined by gas chromatography.

The performance of the catalysts was determined on the basis of the weight of butane fed to the reactor, amount of maleic anhydride (MA) recovered in the wash-water (acidimetry) and amount of butane in the off-gases (volume and concentration) during a specified period of time as:

$$\text{Conversion: } C = \frac{\text{Moles n-butane reacted}}{\text{Moles of n-butane fed}}$$

$$\text{Selectivity: } S = \frac{\text{Moles of MA produced}}{\text{Moles of n-butane reacted}}$$

$$\text{Yield: } Y = C \times S$$

In order to provide a basis for comparison, the following conditions were maintained during the activity tests:

Reaction temperature: 390°–425° C.
n-butane conc. in feed: 3.5–4.5 vol%
Air flow rate: 1 L/min measured at STP
Catalyst loaded to reactor: 0.250 Kg A sample of catalyst obtained after step (6) of Example 1 was introduced in the reactor and tested as described here. The reaction conditions and the results are recorded in Table 1.

EXAMPLE 1.A

For comparison purposes, microspherical catalyst obtained after step (3) calcination was used in the activity test according to Example 2. The results are recorded in Table 1.

EXAMPLE 3

This example is a less preferred embodiment in that the catalyst is not calcined prior to treatment.

Preparation was preformed in the conditions of Example 1 with the difference that steps (1–3) were omitted. In step (4), 1000 g of dried VPO complex and 235 g of a paste of hydrated zirconium hydroxide were mixed with 1000 g $H_2O$ and ground as described in Example 1. The microspherical catalyst recovered after step (6) was used for the attrition tests. The activity test was performed as in Example 2. The results are recorded in Table 1.

EXAMPLE 4

In a particularly preferred way of carrying out the manufacture of the catalyst, the procedure outlined in Example 1, steps (1–3) was followed as described.

In step (4), the material fed to the attritor consisted of 500 g catalyst recovered from step (3) and 500 g dried VPO complex obtained according to U.S. Pat. No. 4,085,122 (Example 1), mixed together with 1000 g $H_2O$. The procedure outlined in steps (4–6) was then followed. The resistance to attrition and the chemical performance of the microspherical catalyst which was obtained was tested as outlined before. The results are given in Table 1.

EXAMPLE 5

One thousand grams of dried VPO complex prepared according to U.S. Pat. No. 4,085,122 was mixed with 1000 g $H_2O$ and 138 g of paste of hydrated titanium hydroxide (approx. 88 wt% water content) and introduced into a high intensity ball mill, as in Example 1.

1. Grinding-1—The operation was carried out for one hour at rotation velocity of the shaft of approximately 372 rpm. The dissipation of mechanical energy caused the temperature of the medium to increase within one hour to approximately 80° C. although no heating medium was circulated through the jacket of the attritor. A sample of the slurry showed that no particles existed with diameters larger than 0.5 μm.
2. Recovery—The slurry was removed from the attritor and spray dried. The material recovered was microspherical with diameters of 40-200 μm.
3. Calcination—The spray-dried product was heated gradually to 450° C. and maintained at this temperature for 6 hours. An atmosphere of $N_2$ was maintained in the oven, during the calcination.
4. Grinding-2—500 grams of material recovered from the previous step were mixed with 1000 g $H_2O$ and 500 g dried PVO complex described above and introduced into the attritor. No cooling water was circulated through the jacket. After an initial grinding period to reduce particle size, a solution of 47 g $H_3PO_4$ (85%) in 300 g of water was added. After three hours of operation, a sample of the slurry showed that all particles had sizes under 0.5 μm.
5. The slurry was drained from the attritor and spray dried. The microspherical material with diameters of 40—200 μm was recovered and submitted to step (6), which is calcination at the conditions described for step (3). The resistance to attrition and the chemical performance of the microspherical catalyst was tested as described before—the results are given in Table 1.

to obtain a variation of the catalyst activity, and the resistance to attrition, by adjusting the amounts of calcined and uncalcined precursor present in the mixture which is subjected to the treatment with acid, preferably a phosphoric acid.

TABLE 2

| | | | Example 7 | | | |
|---|---|---|---|---|---|---|
| Example N° | Hydrocarbon | Temp. (°C.) | Hydrocarbon concentration in feed (vol %) | Hydrocarbon conversion (mol %) | Selectivity to MA (mol %) | MA Yield mol % |
| 8 | 1-butene | 400 | 4.2 | 98.0 | 56.1 | 55.0 |
| 9 | trans-2-butene | 401 | 4.1 | 98.8 | 57.4 | 56.7 |
| 10 | 1,4-butadiene | 390 | 4.5 | 100 | 58.5 | 58.5 |
| 11 | C4 cut (75% n-butenes) | 403 | 4.8 | 99.2* | 59.8* | 44.5** |

*based on n-butenes.
**based on C4 cut.

These and other advantages should be apparent to those skilled in the art from the teachings herein.

Numerous modifications and variations of the present invention are possible in light of the above teachings and, therefore, within the scope of the appended claims,

TABLE 1

| Example No. | AR | Surface Area m²/g | Temp. °C. | n-Butane in Feed, Vol % | Conversion % | Selectivity Mole % | Yield Mole % | Phosphorus/Vanadium |
|---|---|---|---|---|---|---|---|---|
| 1 | 3 | 10 | 406 | 3.5 | 74.8 | 60.5 | 45.3 | 1.13 |
| 1.A | 41 | 30 | 409 | 3.5 | 76.3 | 61. | 47.3 | 1.13 |
| 3 | 26 | 20 | 390 | 3.5 | 56.0 | 71.2 | 39.9 | 1.13 |
| 4 | 6 | 26 | 398 | 3.5 | 77.7 | 58.4 | 44.4 | 1.13' |
| 5 | 8 | 23 | 395 | 3.8 | 77.2 | 57.0 | 44.0 | 1.16 |
| 6 | 4 | 19 | 425 | 4.0 | 69.0 | 65.3 | 45.1 | 1.16 |
| 7 | 6 | 26 | 407 | 4.6 | 81.8 | 70.7 | 57.8 | 1.16 |

Note
P/V: atomic ratio Phosphorus/Vanadium

EXAMPLE 6

A catalyst was prepared in the same manner and with the same ingredients as that of Example 5 with the only difference that the addition of the paste of hydrated titanium hydroxide in the first step was omitted. The attrition resistance and the catalytic performance are reported in Table 1.

EXAMPLE 7-11

The performance of the catalyst prepared according to Example 4 was tested further. In a metal reactor with an internal diameter of 5.1 cm, 1000 g of microspherical catalyst were introduced. In the conditions of the reaction, the height of the fluid bed was approximately 60 cm. The reactor was provided with internal gas redistributing devices. The results of the test with different feeds are recorded in Table 2, as Examples 8, 9, 10 & 11.

The present invention is particularly advantageous in that it is possible to provide an unsupported catalyst comprising mixed oxides of vanadium and phosphorus which is highly resistant to attrition, and which has the requisite catalyst activity for accomplishing oxidation reactions, and in particular, oxidation of hydrocarbon to maleic anhydride. The high resistance to attrition may be accomplished without the addition of additives not normally present in such catalysts. Moreover, by proceeding in accordance with the invention, it is possible the invention may be practiced otherwise than as particularly described.

What is claimed is:
1. A catalyst, comprising:
   mixed oxides of vanadium and phosphorus, said catalyst having a phosphorus to vanadium ratio of from 1:1 to 2:1, said catalyst having been pretreated by contacting a dried catalyst precursor comprising mixed oxides of vanadium and phosphorus, in finely divided form, with an acid solution and drying of the acid treated particles to produce a dried catalyst.
2. The catalyst of claim 1 wherein the finely divided catalyst precursor has an average particle size of less than 10 microns.
3. The catalyst of claim 2 wherein the acid is at least one phosphoric acid.
4. The catalyst of claim 3 wherein at least a portion of the catalyst precursor prior to acid treatment has been calcined to remove water of hydration and provide a partial oxidation of vanadium to the pentavalent state.
5. The catalyst of claim 3 wherein uncalcined catalyst precursor, in finely divided form, is subjected to the acid treatment.
6. The catalyst of claim 3 wherein the catalyst precursor, in finely divided form, which is subjected to acid treatment is a mixture of calcined and uncalcined cata- lyst precursor, the ratio of calcined to uncalcined catalyst precursor in such mixture being from 10:1 to 1:10.

7. The catalyst of claim 6 wherein the dried catalyst has an average particle size of at least 40 microns.

8. The catalyst of claim 7 wherein the dried catalyst is microspherical, and has an average particle size of from 40 to 200 microns.

9. The catalyst of claim 2 wherein the catalyst precursor, in finely divided form, which is subjected to acid treatment is a mixture of calcined and uncalcined precursor, wherein the ratio of calcined precursor to uncalcined precursor is from 10:1 to 1:10.

10. The catalyst of claim 9 wherein the dried catalyst is in microspherical form, and has an average particle size of from 40 to 200 microns.

11. The catalyst of claim 1 wherein the catalyst is in a form, and has a resistance to attrition suitable for use in a fluidized bed.

12. The catalyst of claim 8 wherein the catalyst has a phosphorus to vanadium ratio of from 1:1 to 1.3:1.

13. In a process for preparing a catalyst comprising the mixed oxides of vanadium and phosphorus wherein the phosphorus to vanadium ratio is from 1:1 to 2:1, the improvement comprising:

treating a dried catalyst precursor comprising mixed oxides of vanadium and phosphorus, in finely divided form, with an acid solution; and drying of the acid treated catalyst precursor to produce said catalyst.

14. The process of claim 13 wherein the finely divided catalyst precursor has an average particle size of less than 10 microns.

15. The process of claim 14 wherein the acid is at least one phosphoric acid.

16. The process of claim 15 wherein the finely divided catalyst precursor which is subjected to treatment with acid is a mixture of calcined and uncalcined catalyst wherein the ratio of calcined to uncalcined catalyst is from 1:10 to 10:1.

17. The process of claim 16 wherein the acid treated catalyst precursor is dried to produce a catalyst having a particle size of at least 40 microns.

18. The process of claim 17 wherein the acid treated catalyst precursor is spray dried to produce microspherical catalyst particles having an average particle size of from 40 to 200 microns.

19. A process for producing a catalyst comprising mixed oxides of vanadium and phosphorus suitable for use in a fluidized bed, comprising:

calcining uncalcined catalyst precursor comprising mixed oxides of vanadium and phosphorus to remove water of hydration and provide a partial oxidation of vanadium to the pentavalent state; providing a mixture of uncalcined dried catalyst precursor and the calcined dried catalyst precursor, in finely divided form, said mixture having an average particle size of less than 10 microns; treating said mixture with a solution of at least one phosphoric acid; drying the treated mixture to produce a (treated) dried catalyst having an average particle size of at least 40 microns; and calcining said dried catalyst.

20. The process of claim 19 wherein the mixture of calcined and uncalcined catalyst precursor which is treated with phosphoric acid has a calcined to uncalcined catalyst precursor ratio of from 1:10 to 10:1.

21. The process of claim 20 wherein the drying of the treated mixture is by spray drying to produce microspherical catalyst particles having an average particle size of from 40 to 200 microns.

* * * * *